(12) United States Patent
Shih et al.

(10) Patent No.: US 8,129,188 B2
(45) Date of Patent: Mar. 6, 2012

(54) CELL CULTURE APPARATUS AND METHOD OF FABRICATING THE APPARATUS

(75) Inventors: Ming-Cheng Shih, Taichung (TW); Chin-Fu Chen, Sinjhuang (TW); Rung-Jiun Gau, Kaohsiung (TW); Yu-Shih Weng, Pingtung (TW); Ya-Jen Yu, Taipei (TW); Shao-Jen Yeh, Jhongpu Township, Chiayi County (TW)

(73) Assignee: Industrial Technology Research Institute, Hsinchu (TW)

( * ) Notice: Subject to any disclaimer, the term of this patent is extended or adjusted under 35 U.S.C. 154(b) by 865 days.

(21) Appl. No.: 12/155,785

(22) Filed: Jun. 10, 2008

(65) Prior Publication Data
US 2009/0004731 A1    Jan. 1, 2009

Related U.S. Application Data

(63) Continuation-in-part of application No. 11/446,207, filed on Jun. 5, 2006, now Pat. No. 7,749,761.

(30) Foreign Application Priority Data

Sep. 29, 2005   (TW) ................................ 94133977 A

(51) Int. Cl.
    *C12N 5/07*      (2010.01)
    *C12N 11/08*     (2006.01)
    *C12M 1/00*      (2006.01)

(52) U.S. Cl. ...... 435/397; 435/180; 435/325; 435/283.1
(58) Field of Classification Search ........................ None
    See application file for complete search history.

(56) References Cited

U.S. PATENT DOCUMENTS

| 4,565,784 | A  | * | 1/1986  | Franzblau et al. | 435/397 |
|-----------|----|---|---------|------------------|---------|
| 5,134,057 | A  | * | 7/1992  | Kuypers et al.   | 430/325 |
| 6,770,721 | B1 | * | 8/2004  | Kim              | 526/329 |
| 6,905,738 | B2 | * | 6/2005  | Ringeisen et al. | 427/596 |
| 7,045,366 | B2 | * | 5/2006  | Huang et al.     | 436/529 |
| 7,276,367 | B2 | * | 10/2007 | Ravin et al.     | 435/284.1 |
| 7,371,400 | B2 | * | 5/2008  | Borenstein et al.| 424/423 |
| 7,407,799 | B2 | * | 8/2008  | Balagadde et al. | 435/289.1 |
| 7,695,967 | B1 | * | 4/2010  | Russell et al.   | 435/401 |
| 7,846,727 | B2 | * | 12/2010 | Nishiguchi et al.| 435/395 |

\* cited by examiner

*Primary Examiner* — David Naff
(74) *Attorney, Agent, or Firm* — Bacon & Thomas, PLLC

(57) ABSTRACT

A cell culture apparatus and a method for fabricating the cell culture apparatus are disclosed, the method comprises forming at least one fillister on a biomaterial composite layer by photolithography, wherein the biomaterial composite layer contains two gel materials. One is a bio-compatible hydrogel composition having various weight ratio of: 2-hydroxyethyl-mathacrylate (HEMA), bisphenol A and glycidyl methacrylate (bis-GMA), triethylene glycol dimethacrylate (TEGDMA), r-methacryloxypropyl trimethoxysilane (MAPTMS), $\alpha,\alpha$-diethoxyacetophenone (DEAP), and the other one is a photo-sensitive silica gel composition.

22 Claims, 6 Drawing Sheets

(a)

(b)

(c)

CELL CULTURE APPARATUS AND METHOD OF FABRICATING THE APPARATUS

RELATED APPLICATIONS

This application is a continuation-in-part (CIP) of U.S. patent application for "Cell culture apparatus and a fabricating method of the same", U.S. application Ser. No. 11/446,207, filed Jun. 5, 2006, now U.S. Pat. No. 7,749,761.

BACKGROUND OF THE INVENTION

1. Field of the Invention

The present invention relates to a cell culture apparatus and the fabricating method of the same, especially to a cell culture apparatus and its fabricating method for cell culturing.

2. Description of Related Art

Conventional cell culture apparatus for in vitro cell culture or bioreactors in laboratories has certain limits in culturing cells for medical uses. Those apparatus, cell culture dish, for example, are not ideal for preserving physiological function of primary mammalian cells which may attribute to deficient of proper physiological conditions on dish, 3D microenvironment and mass transfer system, for example. For most apparatus for cell culture in 3D, said conventional bioreactors, are mostly developed for batch mass production of biologics, recombinant proteins, for examples which demand large volume and complicated operating process.

A couple of technologies have been developed to provide 3D environment of cell in vitro. Preconfigured scaffold made from biomaterials and collagen sponge, for example, provide not only mechanical strength but nutrients deposition which facilitate cell growth and metobolites in 3D form in vitro. Those scaffold, or term "frame", for cell culture, however, mostly fabricated by sol-gel method which has some limitations on practical application of biomedical uses, which could be summarized as follows: (1) Larger pore size of scaffold lead to cell cluster formation. The pore size of the frame made of the sol-gel method is in the range of 50-100 μm. However, the size of a normal cell is in the range of 5-20 μm. In contrast to smaller size of cells, larger pore size of frame will lead to cluster formation of cells inside scaffold. (2) Limitation of physical scale of pore size fabricated by conventional method: the pore size of a cell culture frame produced by conventional methods is limited to 100 μm, and the precise shape of the frame is not easy to be re-produced due to poor mechanical strength of biomaterials. (3) Poor mass transformation of nutrients in scaffold. Scaffold in bulk form could lead to insufficient nutrients exchange from cell culture medium through inner scaffold which may result in cell apoptosis in inner part of scaffold.

Therefore, it is desirable to provide an improved method to mitigate the aforementioned problems.

SUMMARY OF THE INVENTION

A hydrogel composition, comprising: 50-100 wt % of 2-hydroxyethyl mathacrylate (HEMA); 5-30 wt % of triethylene glycol dimethacrylate (TEGDMA); 5-30 wt % of r-methacryloxypropyl trimethoxysilane (MAPT MS); and 5-15 wt % of α,α-diethoxyacetophenone (DEAP).

The hydrogel composition of the present invention further comprising 5-50 wt % of bisphenol A and glycidyl methacrylate (Bis-GMA).

Another aspect of the present invention is related to a cell culture apparatus comprising: a substrate; and at least one layer of bio-compatible material forming on said substrate, wherein the material is hydrogel composition or photo-sensitive silica gel composition, and a pattern with at least one recess is formed on said layer of bio-compatible material.

Further, a method for fabricating the cell culture apparatus of the present invention is also disclosed. The method comprises the steps of: (a) providing a substrate; (b) forming a layer of bio-compatible hydrogel composition, or photo-sensitive silica gel composition; and (c) forming a pattern of at least one recess on said layer of bio-compatible material by photolithography.

The method for fabricating the cell culture apparatus of the present invention, further comprising the steps of: (d) filling said recess with a sacrificial layer; (e) exposing said recess and rinsing; (f) forming a layer of bio-compatible hydrogel composition, or photo-sensitive silica gel composition; (g) forming a pattern of at least one recess on said layer of bio-compatible material by photolithography; and (h) removing said sacrificial layer.

According to the method of the present invention, a step (b-1) is further comprised between steps (b) and (c). A second substrate is provided on the layer of bio-compatible hydrogel composition or photo-sensitive silica gel composition in step (b-1). Furthermore, a step (a-1) is further comprised between steps (a) and (b). A spacer is provided on the substrate.

Moreover, wherein the steps (d), (e), (f) and (g) can be repeated one to five times as desired.

The material used for the cell culture apparatus have good biocompatible feature. Besides, it is also suitable for manufacturing process of photolithography. Therefore, cell culture apparatus with microfluidic channel can be produced through photolithography in batch through the method of the present invention. Also, the micro-sized (μm) dimension of the cell culture apparatus can be easily controlled. Hence, the cell culture can be re-produced precisely.

Besides, the biocompatible material of the cell culture apparatus has porous structure. Cultured cells can communicate each other by released signals through the porous water gel between different cell culture platforms. The interactions or signal regulations between cells stabilize physical activities of target cells, therefore their lifespan and biological functions can be prolonged.

The present invention also provides a cell culture apparatus, comprising a substrate; and a layer of bio-compatible material forming on said substrate, wherein the material is hydrogel composition or photo-sensitive silica gel composition, and a pattern with at least one recess on said layer of bio-compatible material.

The cell culture apparatus of the present invention is composed with hydrogel composition, which is optionally comprises: bisphenol A and glycidyl methacrylate (Bis-GMA) (viscous material), triethylene glycol dimethacrylate (TEGDMA) (cross linker), r-methacryloxypropyl trimethoxysilane (MAPT MS) (adhesion improving reagent), α,α-diethoxyacetophenone (DEAP) (photo-sensitive agent) or the combinations thereof.

The hydrogel composition preferably comprises: 50-100 weight percentage of 2-hydroxyethyl mathacrylate (HEMA), 0-50 weight percentage, preferably 5-50 weight percentage of bisphenol A and glycidyl methacrylate (Bis-GMA), 5-30 weight percentage of triethylene glycol dimethacrylate (TEGDMA), 5-30 weight percentage of r-methacryloxypropyl trimethoxysilane (MAPT MS), and 5-15 weight percentage of α,α-diethoxyacetophenone (DEAP).

In the method of the present invention, the photolithography of step (c) can comprise any step of conventional photolithography. Preferably, the photolithography of step (c) comprises exposure and development. The light source for photolithography can be any conventional light used for curing bio-compatible materials. Preferably, the bio-compatible material is exposed to UV light.

In the method of the present invention, the substrate can be any conventional substrates. More preferably, the substrate is made from transparent or semi-transparent materials. The substrate material is preferably selected from the group consisting of glass, silicon, plastic, rubber, ceramic and the combination thereof.

In the present invention method, the step of development can be performed through any conventional process. Preferably, the bio-compatible material is developed by any developers. And the developer used in the present method can be any solvent used to dissolve bio-compatible materials, e.g., HEMA. Preferably, the solvent is ethanol, acetone or the mixture thereof. The recess formed on the bio-compatible material can be of any pattern. Preferably, the recess is at least one microfluidic channel.

The width of the microfluidic channel is preferably in a range from 1 μm to 1000 μm, and more preferably is between 1 μm to 100 μm. The material of the sacrificial layer used in the present method is 2-acrylamido-2-methyl-propane-sulfonic acid (AMPS), N-isopropyl-acrylamide (NiPAAm) or methacrylic acid (MAA). Preferably, the material of the sacrificial layer is AMPS.

The step (h) in the method of the present invention is preferably achieved by water rinsing. The step (a) is performed by any known process. Preferably, the step (a) is performed by spin coating. The bio-compatible material exposed to UV light undergoes a photo-curing reaction. Preferably, the photo-curing reaction is polymerization.

The bio-compatible material is photo-cured to obtain a micro structure through a photolithography process, such as UV exposure. The micro structure operates in coordination with the pattern of microfluidic channels is so-called a cell micro patterning. The main feature of the cell culture apparatus of the present invention is optionally of a porous or non-porous configuration. The main material of the cell culture apparatus depends on the purposes of cell interaction or cell isolation.

A three dimensional scaffold of the cell culture apparatus is obtained through repeated steps of exposure and development. Different cell lines can have different distributions by simply controlling the flow of microfluid, The cell micro patterning in the cell culture apparatus thus can be obtained. Therefore, the cell culture environment or physical tissue structure in the present cell culture apparatus is more imitative to those in vivo by controlling the distribution or combination of different cells.

Moreover, the water gel composition and the photosensitive silicon composition are transparent or semi-transparent materials. Therefore, it is suitable for embedding the culture plate and proceeding tissue section other than monitoring the lysed bio-molecules.

Furthermore, the cell culture apparatus of the present invention can be connected or equipped with existing microscope systems directly for monitoring in real time.

Other objects, advantages, and novel features of the invention will become more apparent from the following detailed description when taken in conjunction with the accompanying drawings.

DETAILED DESCRIPTION OF THE PREFERRED EMBODIMENT

Example 1

The material of the cell culture apparatus of the present invention is a high biocompatible material such as 2-hydroxyethyl mathacrylate (HEMA). The material is optionally combined with viscous material, cross-linker, adhesion improving reagent and photo-sensitive agent. The biocompatible material is photo-cured after exposing to UV light, and the cured material can be adhered well to the substrate of the cell culture substrate.

The biocompatible material of water gel composition of the present invention comprises: 50-100 weight percentage of 2-hydroxyethyl mathacrylate (HEMA), 0-50 weight percentage, preferably 5-50 weight percentage of phenol A and glycidyl methacrylate (Bis-GMA), 5-30 weight percentage of triethylene glycol dimethacrylate (TEGDMA), 5-30 weight percentage of r-methacryloxypropyl trimethoxysilane (MAPT MS), and 5-15 weight percentage of α,α-diethoxyacetophenone (DEAP).

Figure 1:
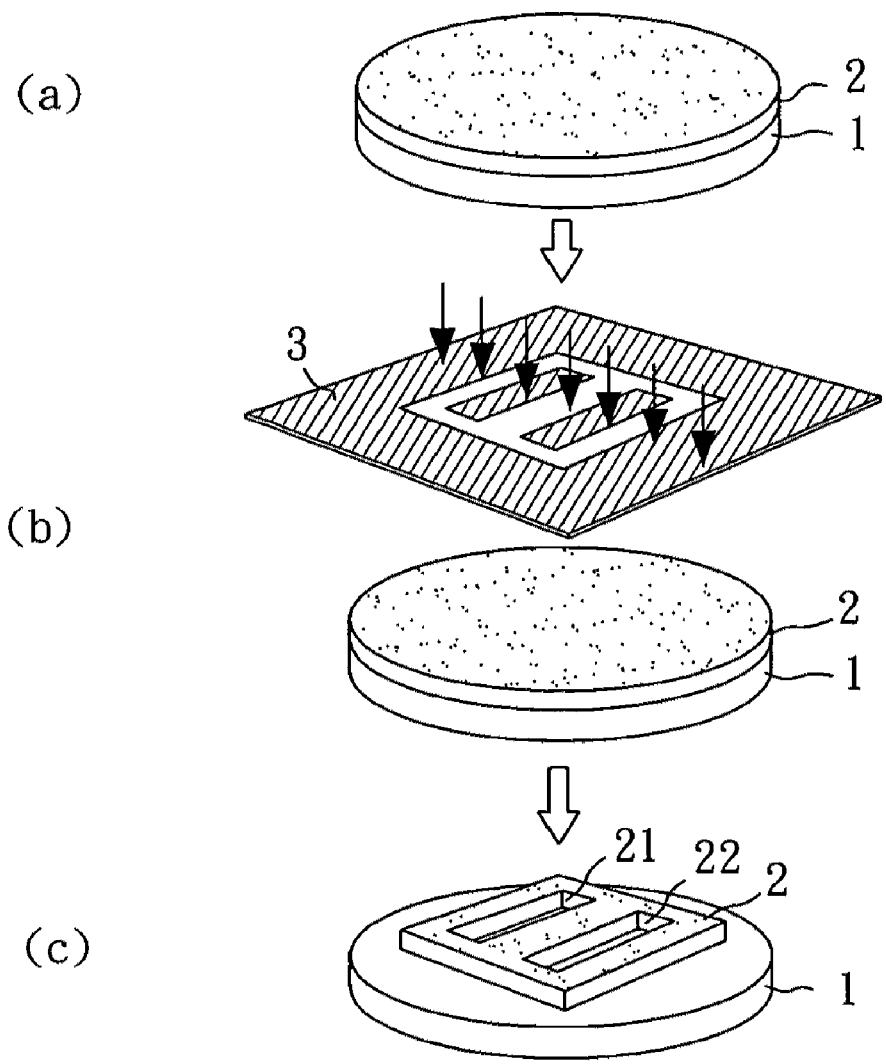
FIG. 1(a)-(c) illustrates the flowchart of the fabricating method of the cell culture apparatus in example 1.

The main material of the cell culture apparatus is HEMA. The Bis-GMA is used as viscous material. TEGDMA acts as the cross-linker, MAPTMS is the adhesion improving reagent, and DEAP is the photosensitive agent. The photosensitive agent in the HEMA can be cured by polymerization through UV light exposure. FIGS. 1(a)-(c) illustrate the flowchart of the fabricating method of the cell culture apparatus of the present embodiment. First, a substrate 1 is provided, and the substrate material is selected from the group consisting of glass, silicon, plastic, rubber, ceramic and the combination thereof. The biocompatible adhesion-improving reagent of the correlative substrate material is alkoxysilanes, halosilanes, alkylthiols, or alkylphosphonates. In the present embodiment, the substrate material is glass, and the adhesion-improving reagent is MAPTMS.

Second, a layer of biocompatible material is formed on the substrate 1. In the present embodiment, a first material layer 2 is formed on the substrate 1 by spin coating. The biocompatible material used in the present embodiment comprises: 5 wt % of HEMA, 4 wt % of Bis-GMA, 2.7 wt % of TEGDMA, 2.7 wt % of MAPTMS, and 1.35 wt % of DEAP.

Then, a pattern is formed on the first material layer 2 through photolithography. As shown in FIG. 1(b), a photomask 3 is aligned over the first material layer 2 to perform exposure. The first material layer 2 exposed to UV light undergoes polymerization and becomes insoluble in the developer. On the contrary, non-exposed portion of the first material layer 2 is not polymerized, meanwhile, the HEMA exists in the form of monomer and it remains soluble in the developer.

Finally, non-exposed portion is removed by the developer, and the molded microfluidic channels defined by the photomask is obtained on the first material layer 2. The light for exposure in the present invention can be any conventional light used for curing the biocompatible material in the present invention. The developer can be any conventional solvent to remove uncured biocompatible material in the present invention. In the present embodiment, the first material layer 2 is exposed to UV light (365 nm, 100 W/cm²) for 60 seconds with the photomask 3. A developer containing acetone and ethanol in a ratio of 50:50 is used to remove uncured biocompatible material. A layer of micropattern is formed, and it is used as the platform for cell culturing, as shown in FIG. 1(c).

The micropattern of the cell culture apparatus of the present invention have at least one recess 21. The forming process of the recess 21 is different with various patterns of photomasks and the process of photolithography. The size of micropattern is various by different photomasks. In the present embodiment, the micropattern is a microfluidic channel with a width of 5 μm.

Figure 2:
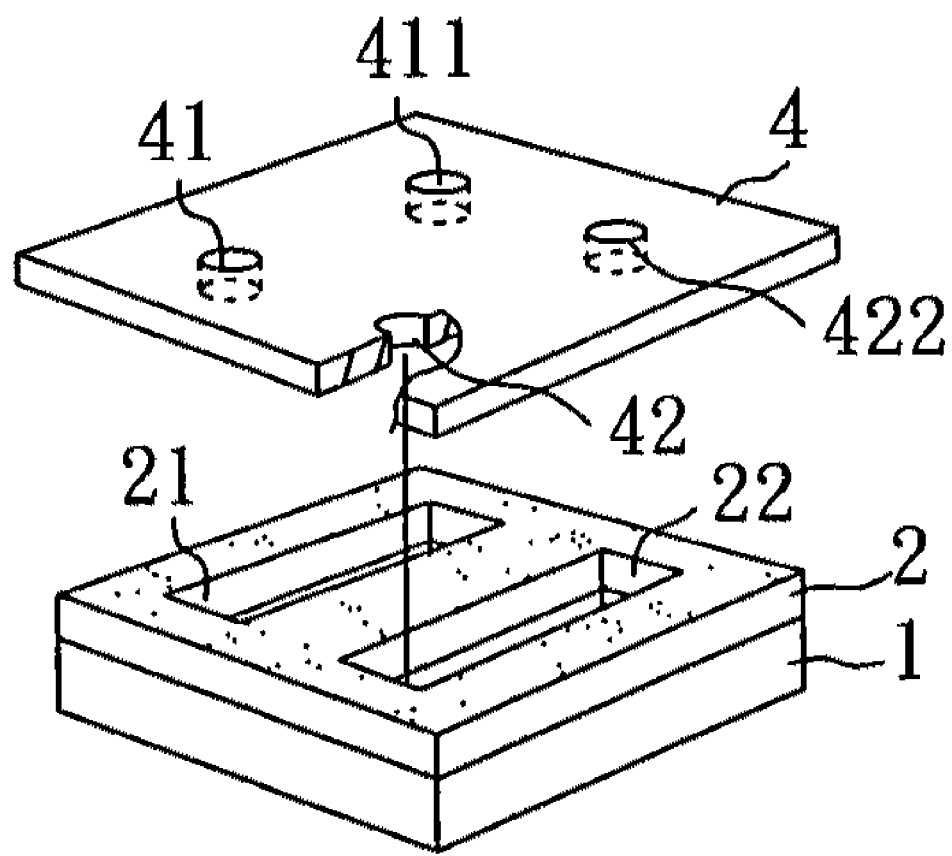
FIG. 2 is a diagram illustrating the structure of the cell culture apparatus in example 1 of the present invention.

Cells with the same or different phenotypes can be cultured in the same cell culture apparatus of the present invention. As it is shown in FIG. 2, an upper cover 4 is formed with a soft material, such as silicon. There forms an inlet hole 41 and an outlet hole 411 on the upper cover 4 for cells flowing. Then, the upper cover 4 is contact with the first material layer 2 tightly, and the inlet hole 41 of the upper cover 4 is connected to the recess 21 of the first material layer 2. Cells are applied into to the recess 21 of the first material layer 2 through the inlet hole 41. The cells are retained in the bottom of the recess 21 (the surface of the substrate 1). Circulating culture media is then applied after the cells attached completely. Similarly, the other recess 22 is used for cell culturing by applying cells and culture media through inlet 42 and outlet 422. The cells culture in the recess 21 and recess 22 can be different or the same.

Figure 4:
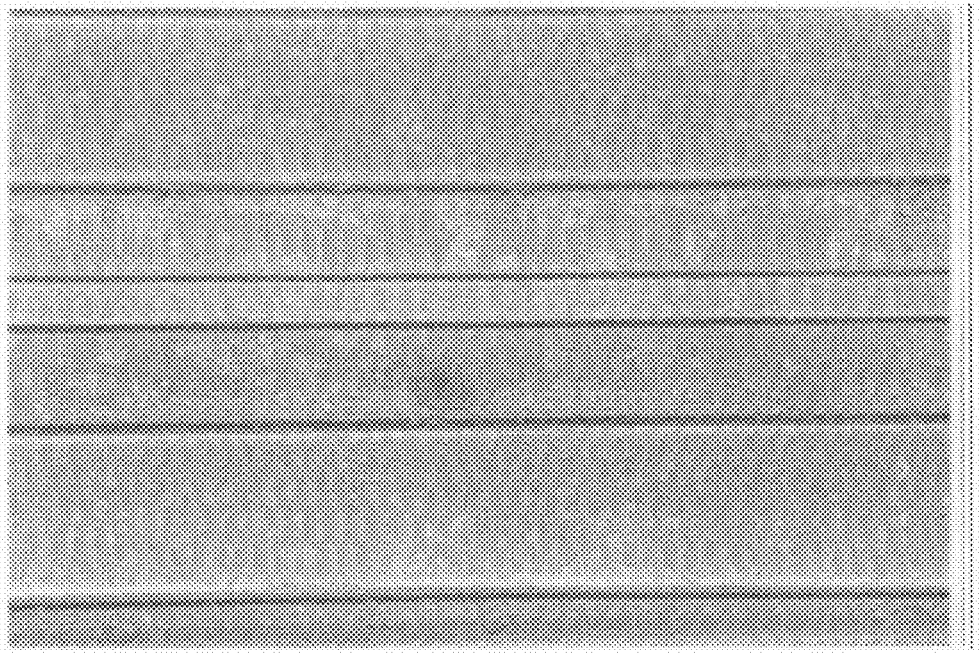
FIG. 4 is the photo of cultured cells in example 1.

FIG. 4 shows the photo of cultured cells. The condition for cell culturing is: (1) rinsing the culture plate with micropattern with PBS solution twice; (2) suspending $5 \times 10^5$ cells/ml of CA 3 cells in MEM culture medium containing 10% FBS, then seeding the cells into the culture plate for one-day culturing; (3) removing the culture medium and rinsing the plate with PBS for twice, for removing un-attached cells or non-clustered cells. Then, keep monitoring the condition of cell growing.

The cell culture apparatus can be used to monitor the lysed bio-molecules. Moreover, it is suitable for embedding the culture plate and proceeding tissue section, because the HEMA composition and the photosensitive silicon composition are transparent. The biocompatible material used in the present invention is a porous water gel (HEMA). The biological signals (e.g. proteins) released from a cell can be transmitted to another surrounding cell through the porous microstructure. Therefore, the purpose of co-culturing cells achieves. The problem of low growth rate in culturing isolated liver cells in vitro can also be solved. Furthermore, the cell culture apparatus of the present invention performs various combinations of cell lines. It imitates more closely to a real human tissue since the real tissue is composed with multiple cell lines.

Figure 3:
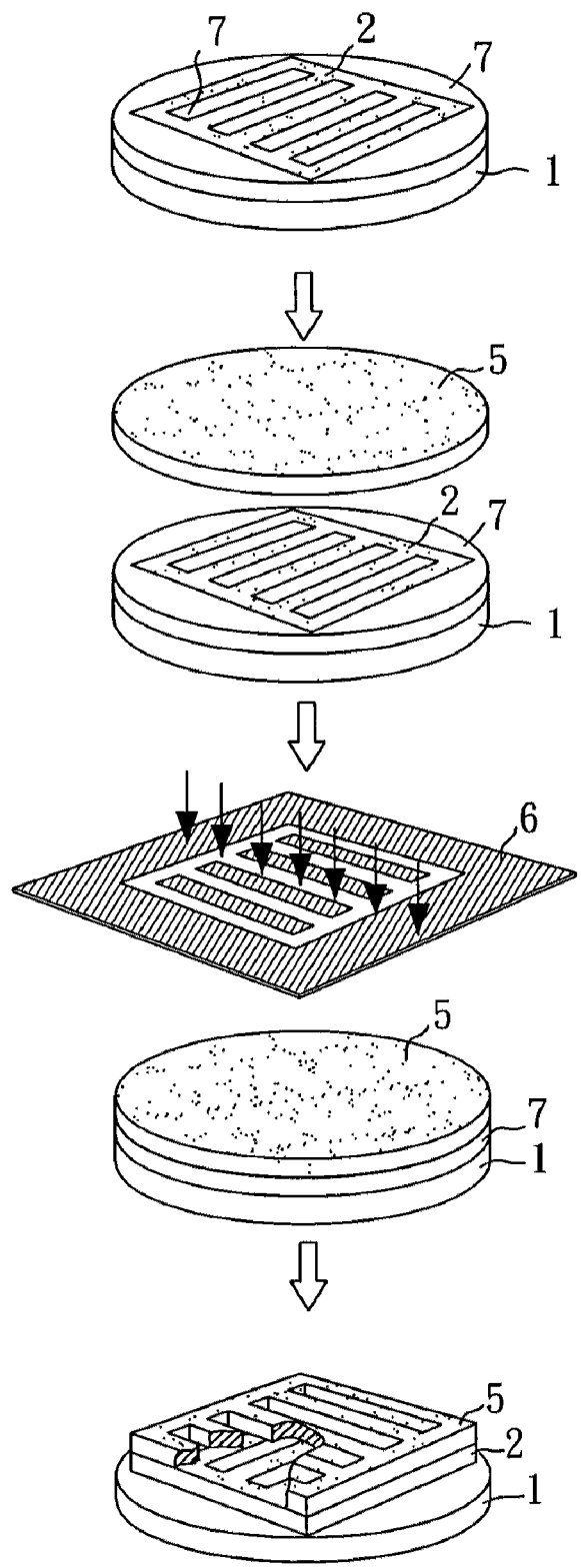
FIG. 3 is a flow chart of another embodiment in example 2 of the present invention method.

Another embodiment is shown in FIG. 3. The multiple culture layers can be prepared following the method described above. A three-dimensional cell scaffold is formed via spin coating and photolithography. The recesses 21, 22 on the single layer of cell culture platform, as shown in FIG. 1(c), are filled with a sacrificial layer 7. Steps of spin coating and photolithography are repeated to form the second material layer 5. Then, another photomask 6 is aligned to the second material layer 5, and the second material layer 5 is exposed to UV light. Polymerization is introduced in the exposed portion of the second material layer 5. The portion of non-exposed second material layer 5 is then removed by a developer. Thus, a micropattern is formed. In the present embodiment, the micropattern is a microfluidic channel, which has at least one groove with width of 5 μm. Finally, the sacrificial layer 7 is removed. And a three dimensional scaffold of multiple cell culture platforms with network pattern is created. In the present embodiment, the material of the sacrificial layer is AMPS, and it is removed by water rinsing.

Example 2

The material of the cell culture apparatus of the present invention can be a photosensitive silicon composition in place of HEMA composition.

The process is the same as described in example 1. A glass substrate 1 is provided as shown in FIG. 1(a). About 3 ml of patternable silicon rubber (Corning, WL-5350) is applied onto the glass substrate 1. The glass substrate 1 is spun on a spin coater in 500 rpm for 30 seconds, and a first material layer 2 with 50 μm thickness is formed. Then, the glass substrate is placed on the hot plate for soft baking under 110° C.-120° C.

Refer to FIG. 1(b). The silicon rubber (the first material layer 2) is exposed to UV light (600-1000 mJ/cm²) in an exposure. The post exposure baking is performed on the glass substrate on the hot plate under 150° C. Subsequently, the cell culture platform is created after developing for one hour by a negative develop reagent, as shown in FIG. 1(c).

Figure 5:
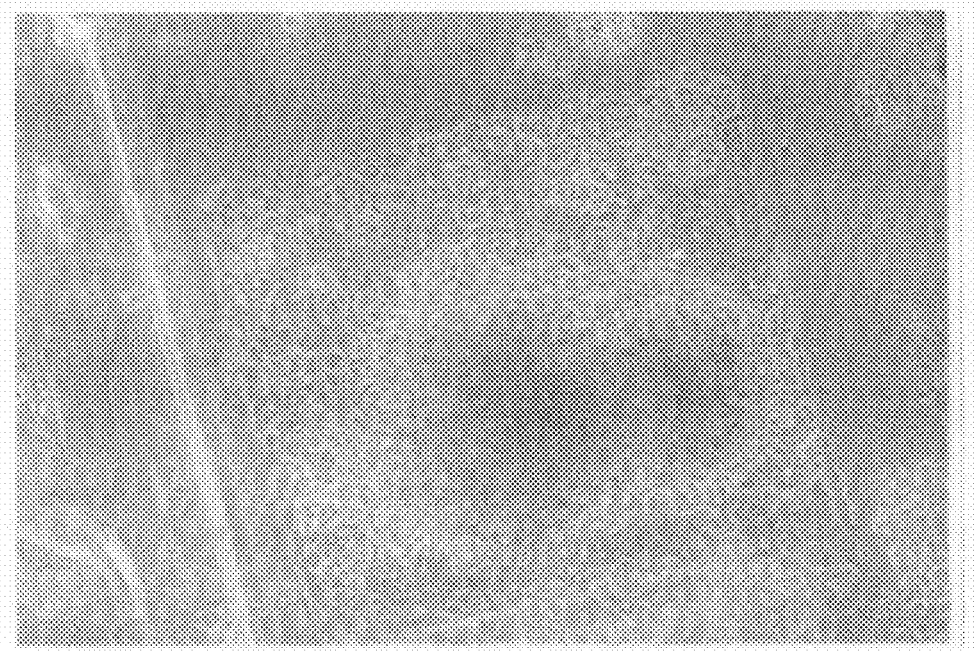
FIG. 5 is the photo of cultured cells in example 2.

FIG. 5 shows the photo of cultured cell of the present embodiment, and the condition is the same as described in example 1.

Example 3

The example illustrates the method for manufacturing the cell culture apparatus. The microfluidic channel can be formed as well as to bond the upper substrate and the lower substrate together. Therefore, the manufacturing steps and time consuming are saved. The material used in the present example is a biocompatible material, for example, HEMA. Optionally, the viscous material, cross-linker, adhesion improving reagent, and the photosensitive agent are further included. The bio-compatible material is cured after exposed to UV light, moreover, the cured material is adhered well to the substrate of the cell culture apparatus.

The biocompatible material of water gel composition of the present invention comprises the same material as described in example 1: 50-100 weight percentage of 2-hydroxyethyl mathacrylate (HEMA), 0-50 weight percentage, preferably 5-50 weight percentage of phenol A and glycidyl methacrylate (Bis-GMA), 5-30 weight percentage of triethylene glycol dimethacrylate (TEGDMA), 5-30 weight percentage of r-methacryloxypropyl trimethoxysilane (MAPT MS), and 5-15 weight percentage of α,α-diethoxyacetophenone (DEAP).

Figure 6:
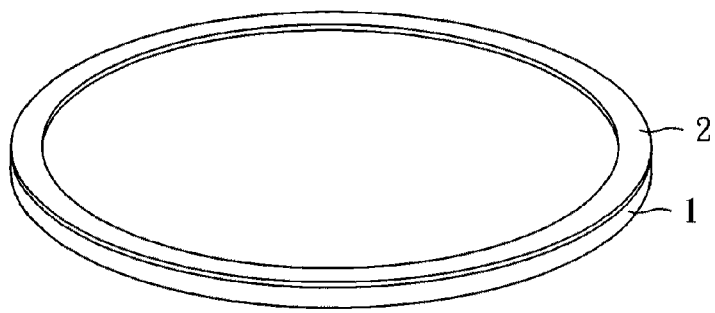
FIGS. 6(a)-(c) illustrate the flowchart of the fabricating method of the cell culture apparatus in example 3.
Figure 6:
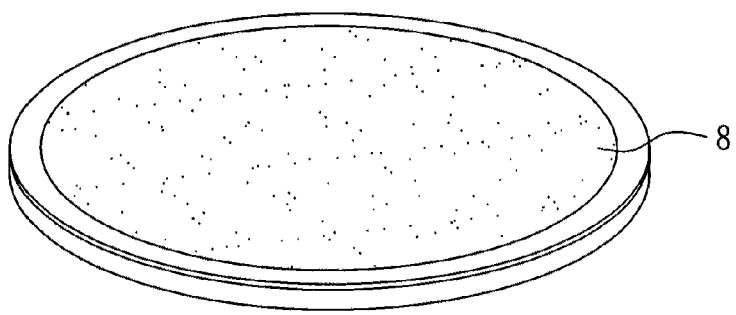
Figure 6:
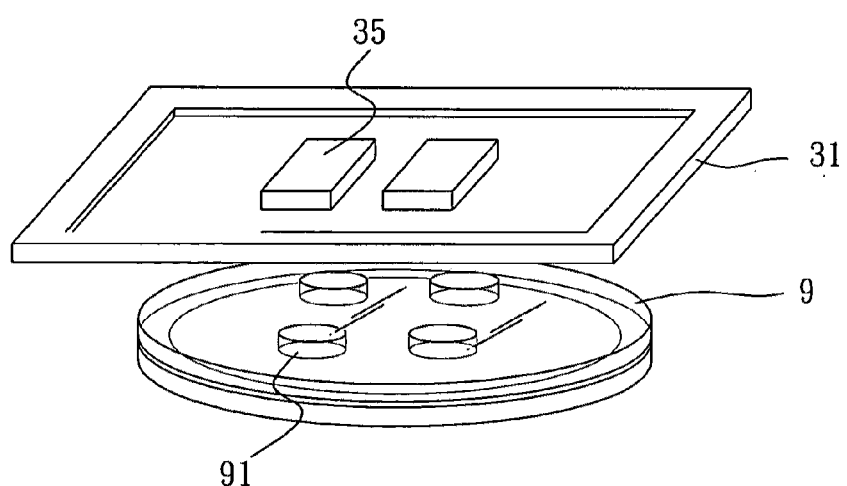
Figure 7:
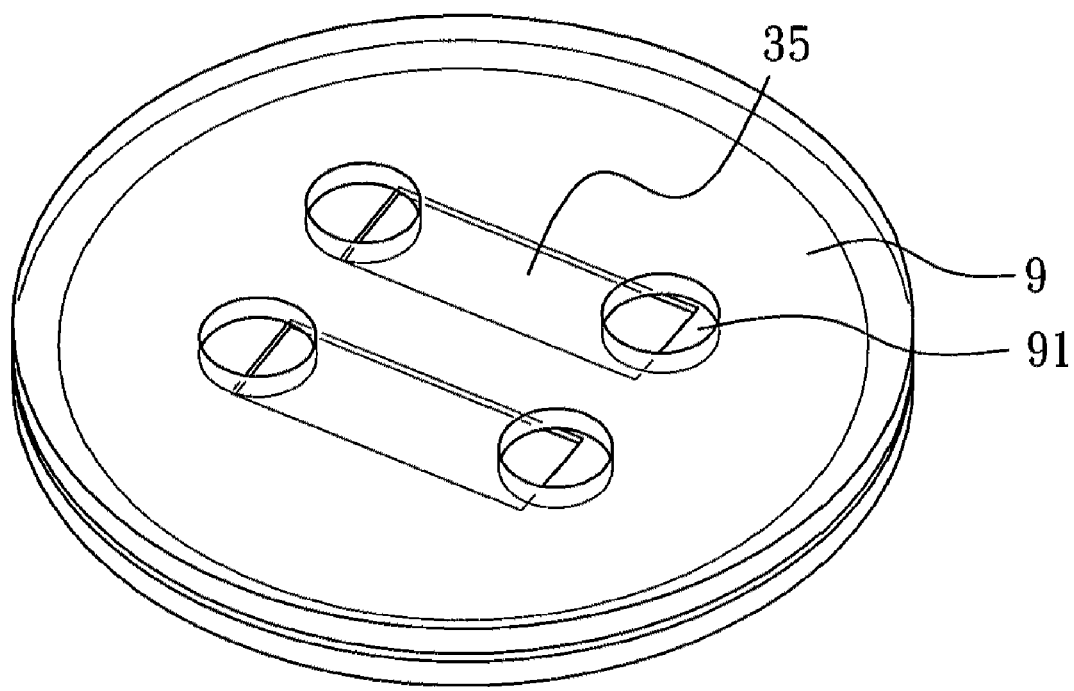
FIG. 7 is a diagram illustrating the structure of the cell culture apparatus in example 3.

The main material of the cell culture apparatus is HEMA. The Bis-GMA is used as a viscous material. TEGDMA acts as the cross-linker, MAPTMS is the adhesion improving reagent, and DEAP is the photosensitive agent. The photosensitive agent in the HEMA can be cured by polymerization through UV light exposure. FIG. 6(a)-(c) illustrates the flowchart of the fabricating method of the cell culture apparatus of the present embodiment. First, a substrate 1 is provided, and the substrate material is selected from the group consisting of glass, silicon, plastic, rubber, ceramic and the combination thereof. And the biocompatible adhesion-improving reagent of the correlative substrate material is alkoxysilanes, halosilanes, alkylthiols, or alkylphosphsnates. In the present embodiment, the substrate material is glass, and the adhesion-improving reagent is MAPTMS.

A first material layer 2 is formed over the substrate 1 by spin coating in the present example. The first material layer 2 is a photoresist, and a structure with predetermined height is formed at the edge of the substrate after photolithography. The height of the next layer of biocompatible material can thus be controlled. As shown in FIG. 6(b), a layer of biocompatible material 8 is formed on the first material layer 2 and the substrate 1 by spin coating. The biocompatible material used in the present embodiment comprises: 5 wt % of HEMA, 4 wt % of Bis-GMA, 2.7 wt % of TEGDMA, 2.7 wt % of MAPTMS, and 1.35 wt % of DEAP.

Then, an upper cover 9 with patterns (pores 91) is stacked on the first material layer 2. Press the layer of biocompatible material 8 to regulate the thickness of the structure between the upper and the lower layers. A photomask 31 having a pattern 35 is aligned to the pores 91 on the upper cover 9, and the beginning of the fluid path on the pattern 35 is aligned to the pores 41 to perform exposure. During the photolithography with UV light, polymerization is introduced in the exposed portion of the layer of biocompatible material 8, where the region would not be removed by the developer. On the contrary, the HEMA material on the portion of non-exposed biocompatible material layer 8 is then removed by a developer because HEMA still remains in monomer.

Finally, non-exposed portion is removed by the developer, and the pattern of molded microfluidic channels 35 defined by the photomask 31 is obtained on the surface of substrate 1 and that of the upper cover 9. The light source for exposure in the present invention can be any conventional light source used for curing the biocompatible material in the present invention. The developer can be any conventional solvent to remove uncured biocompatible material in the present invention. In the present embodiment, the biocompatible material layer 3 is exposed to UV light (365 nm, 100 W/cm$^2$) for 70 seconds through the photomask 5. A developer containing acetone and ethanol in a ratio of 50:50 is used to remove uncured biocompatible material. A cell culture apparatus with micropattern is formed between the substrate 1 and the upper cover 9.

It spends less time in fabricating the cell culture apparatus of the present invention. The structure dimension with micro-size can be controlled precisely, and can be batch re-produced, because the micropattern is formed via photolithography. Besides, since the biocompatible material HEMA forms a porous water gel, cells can communicate each other by released signals through the porous water gel between different cell culture platforms.

In the conventional techniques, the materials used for preparing micropattern via photolithography are PDMS, PEG or other materials without biocompatible feature.

The present invention provides a method for fabricating a multiple-used cell culture apparatus, and it can be produced in large quantity. The apparatus also provides a microenvironment, which closely imitates a native cell environment for a better monitoring of cell metabolism in vitro. In addition, the cell culture apparatus can combine with automatic systems for high throughput and high content drug candidate screening.

Although the present invention has been explained in relation to its preferred embodiment, it is to be understood that many other possible modifications and variations can be made without departing from the spirit and scope of the invention as hereinafter claimed.

What is claimed is:

1. A cell culture apparatus, comprising:
   a substrate; and
   at least one layer of a bio-compatible hydrogel composition formed in a pattern having at least one recess on said substrate,
   wherein the bio-compatible hydrogel composition comprises: 50-85 wt % of 2-hydroxyethyl methacrylate (HEMA); 5-30 wt % of triethylene glycol dimethacrylate (TEGDMA); 5-30 wt % of r-methacryloxypropyl trimethoxysilane (MAPT MS); and 5-15 wt % of α,α-diethoxyacetophenone (DEAP).

2. The apparatus of claim 1, wherein the substrate is made of transparent or semi-transparent materials.

3. The apparatus of claim 1, wherein the substrate is made of glass, silicon, plastic, rubber, ceramic or a combination thereof.

4. The apparatus of claim 1, wherein the bio-compatible hydrogel composition further comprises:
   5-35 wt % of bisphenol A glycidyl methacrylate (Bis-GMA).

5. The apparatus of claim 1, wherein the pattern is formed by photolithography.

6. A method for fabricating a cell culture apparatus, comprising the steps of:
   (a) providing a first substrate;
   (b) forming a first layer of a bio-compatible hydrogel composition on the first substrate, wherein the bio-compatible hydrogel composition comprises: 50-85 wt % of 2-hydroxyethyl methacrylate (HEMA); 5-30 wt % of triethylene glycol dimethacrylate (TEGDMA); 5-30 wt % of r-methacryloxypropyl trimethoxysilane (MAPT MS); and 5-15 wt % of α,α-diethoxyacetophenone (DEAP); and
   (c) forming the first layer of the bio-compatible hydrogel composition in a pattern having at least one recess by photolithography.

7. The method of claim 6, further comprising a step (b-1) between the steps (b) and (c): providing a second substrate on the first layer of the bio-compatible hydrogel composition.

8. The method of claim 6, further comprising the steps of:
   (d) filling said recess of said first layer of step (c) with a sacrificial layer;
   (e) forming a second layer of the bio-compatible hydrogel composition on said first layer of step (d);
   (f) forming said second layer in a pattern having at least one recess by photolithography; and
   (g) removing said sacrificial layer.

9. The method of claim 8, wherein the steps (d), (e), (f) and (g) are repeated one to five times.

10. The method of claim 6, wherein said photolithography comprises exposure and development.

11. The method of claim 10, wherein the bio-compatible hydrogel composition is exposed to UV light.

12. The method of claim 6, wherein the bio-compatible hydrogel composition is developed by a developer.

13. The method of claim 12, wherein the developer is ethanol, acetone or the mixture thereof.

14. The method of claim 6, wherein the recess is a microfluidic channel.

15. The method of claim 14, wherein the pattern of the microfluidic channel is aligned by a photomask.

16. The method of claim 8, wherein the material of the sacrificial layer is 2-acrylamido-2-methyl-propanesulfonic acid (AMPS) or N-isopropyl-acrylamide (NiPAAm).

17. The method of claim 8, wherein the step (g) is achieved by water rinsing.

18. The method of claim 6, wherein the first layer of the bio-compatible hydrogel composition is formed by spin coating in the step (b).

19. The method of claim 11, wherein polymerization occurs in the bio-compatible hydrogel composition exposed to UV light.

20. The method of claim 7, wherein the first or second substrate is made of transparent or semi-transparent materials.

21. The method of claim 7, wherein the first or second substrate is made of glass, silicon, plastic, rubber, ceramic or a combination thereof.

22. The method of claim 6, wherein the bio-compatible hydrogel composition further comprises:
   5-35 wt % of bisphenol A glycidyl methacrylate (Bis-GMA).

* * * * *